(12) United States Patent
Miyazaki et al.

(10) Patent No.: US 7,688,078 B2
(45) Date of Patent: Mar. 30, 2010

(54) SYSTEM AND METHOD FOR COUNTING NUMBER OF LAYERS OF MULTILAYER OBJECT BY MEANS OF ELECTROMAGNETIC WAVE

(75) Inventors: Jungo Miyazaki, Tokyo (JP); Toshihiko Ouchi, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/566,751

(22) PCT Filed: Nov. 22, 2004

(86) PCT No.: PCT/JP2004/017670

§ 371 (c)(1),
(2), (4) Date: Feb. 1, 2006

(87) PCT Pub. No.: WO2005/052509

PCT Pub. Date: Jun. 9, 2005

(65) Prior Publication Data

US 2006/0244629 A1    Nov. 2, 2006

(30) Foreign Application Priority Data

Nov. 25, 2003  (JP)  ............................. 2003-393248

(51) Int. Cl.
*G01N 22/00* (2006.01)
*G01R 27/04* (2006.01)
*G01V 3/00* (2006.01)

(52) U.S. Cl. ..................... 324/637; 324/644; 324/639; 324/642

(58) Field of Classification Search ................. 324/644, 324/637
See application file for complete search history.

(56) References Cited

U.S. PATENT DOCUMENTS 3,490,037 A    1/1970  Williams ................... 324/58.5

(Continued)

FOREIGN PATENT DOCUMENTS

DE    199 22 125 A1    11/2000

(Continued)

OTHER PUBLICATIONS

Jun Takayanagi, et al., "High-resolution Time-of-Flight Terahertz Tomography Using A Femtosecond Fiber Laser", Optics Express, pp. 7549-7555, vol. 17, No. 9., Apr. 2009.

*Primary Examiner*—Timothy J Dole
*Assistant Examiner*—John Zhu
(74) *Attorney, Agent, or Firm*—Fitzpatrick, Cella Harper & Scinto

(57) ABSTRACT

A system or method for counting the number of layers of a multilayer object is adapted for counting the number of layers by means of a simple arrangement of emitting an electromagnetic wave to strike the object that is in a multilayer state. In the system or method, an electromagnetic wave is caused to strike at least either the top surface or the bottom surface of a multilayer object and electromagnetic waves generated by reflection of the incident electromagnetic wave at the respective interfaces of the layers of the multilayer object or an electromagnetic wave generated by transmission of the electromagnetic wave through the multilayer object.

12 Claims, 7 Drawing Sheets

U.S. PATENT DOCUMENTS

| | | | |
|---|---|---|---|
| 5,086,279 A * | 2/1992 | Wochnowski et al. | 324/637 |
| 5,384,543 A * | 1/1995 | Bible et al. | 324/644 |
| 5,384,715 A * | 1/1995 | Lytton | 702/12 |
| 5,539,322 A * | 7/1996 | Zoughi et al. | 324/644 |
| 5,574,464 A * | 11/1996 | Madonna et al. | 342/198 |
| 5,936,237 A * | 8/1999 | van der Weide | 250/234 |
| 2006/0085159 A1 | 4/2006 | Itsuji et al. | |
| 2006/0085160 A1 | 4/2006 | Ouchi | |
| 2006/0188398 A1 | 8/2006 | Yano et al. | |
| 2006/0197021 A1 | 9/2006 | Ouchi | |
| 2006/0214176 A1 | 9/2006 | Ouchi et al. | |
| 2006/0227340 A1 | 10/2006 | Shioda et al. | |
| 2006/0288756 A1 * | 12/2006 | De Meurechy | 73/1.01 |
| 2007/0030115 A1 | 2/2007 | Itsuji et al. | |

FOREIGN PATENT DOCUMENTS

| | | |
|---|---|---|
| JP | 57 170347 | 10/1982 |
| JP | 06 241763 | 2/1994 |
| JP | 2003-44826 | 2/2003 |

* cited by examiner

US 7,688,078 B2

SYSTEM AND METHOD FOR COUNTING NUMBER OF LAYERS OF MULTILAYER OBJECT BY MEANS OF ELECTROMAGNETIC WAVE

TECHNICAL FIELD

This invention relates to a system and a method for counting the number of layers of an object in a multilayer state (to be also referred to as multilayer object) on the basis of the electromagnetic signal obtained by irradiating at least either the top surface or the bottom surface of the multilayer object with an electromagnetic wave so as to be reflected by or transmitted through the object.

BACKGROUND ART

Some known systems and methods for counting the number of layers of a multilayer object will be described below. FIGS. 9 and 10 illustrate a system and a method that are known for counting the number of layers of a multilayer object formed by laying sheets of a material (Japanese Patent Application Laid-Open No. 2003-44826). FIG. 9 illustrates the configuration of the known counting system. Referring to FIG. 9, the system comprises a first projector 74a for projecting infrared rays that strike a lateral surface of a multilayer object 12 (film) mounted on a reference table 75, a second projector 74b (mounted on a lamp holding plate 72) for irradiating auxiliary light onto the top surface of the film, a third projector 74c for irradiating auxiliary light onto the bottom surface of the film, which projectors are controlled by a lighting unit 73. Infrared rays irradiated from the first projector are transmitted through the film and received by an optical receiver 77. The reception signal that represents the received infrared rays is supplied to a processing unit 78 as image information 81 on the distribution of intensity of the transmitted infrared rays relative to the Z-axis of the coordinate system shown in FIGS. 9 and 10. The processing unit 78 counts the number of layers of the film by detecting the multilayer lines in the image information 81.

FIGS. 11, 12A and 12B illustrate a system and a method that are known for checking the number of cards (Japanese Patent Application Laid-Open No. H06-241763). Referring to FIGS. 12A and 12B, cards 102 having at least a metal foil layer or a metal oxide layer laid on part or all of the surface thereof are rigidly secured to a pasteboard 101 and contained in an envelope 99 in a sealed state with an enclosed object 103. An electromagnetic wave is irradiated from an electromagnetic radiator sensor 91 arranged outside the envelope 99 onto the cards in the envelope 99 and the electromagnetic wave reflected from the cards and the electromagnetic wave transmitted through the cards are detected respectively by a reflected wave receiving sensor 92 and a transmitted wave receiving sensor 93 (FIG. 11) to produce respective output waveforms as shown in FIGS. 12A and 12B, each of which illustrates the change with time of the output voltage value. The output waveforms (reference patterns) obtained from certain numbers (0 to 4) of cards are stored in advance in a primary judging section 94 as shown in FIG. 11 and the number of cards contained in the envelope 99 is judged to be 0, 1, 2, 3 or 4 by the reflected wave sensor and the transmitted wave sensor who compare the detected waveforms with the waveforms of the reference patterns. The number of cards that is detected by the primary judging section 94 is compared with the number of cards that is supposed to be found in the envelope 99 by a secondary judging section 95 as the number of cards that is supposed to be found in the envelope 99 is input from a data base 98 that stores the number in advance or as the number of cards that is supposed to be found in the envelope 99 as recorded (printed) on the pasteboard 101 or the envelope 99 is read by a CCD camera through the window of the envelope immediately before or after the irradiation of the electromagnetic wave and judged by the secondary judging section to agree with each other or not. A normal signal SS is sent to a control section 97 that controls the entire system when the two numbers agree with each other, whereas an abnormal signal ES is sent to the control section 97 when the two numbers do not agree with each other. The checking operation is continued when a normal signal SS is input to the control section 97, whereas an operation of removing the envelope out of the line is conducted when an abnormal signal ES is input to the control section 97. The results of the process of checking the numbers of cards are sequentially recorded in a recording section 96 and a report describing the results is printed out so that the operator can keep the checking process under control so as to make it proceed properly.

DISCLOSURE OF THE INVENTION

However, the above described known system and method for counting the number of sheets of a multilayer object by projecting light to a lateral surface of the object are accompanied by a problem that the performance of the system is affected by the cut surfaces, if any, of the multilayer object. For instance, it is not possible to accurately count the number of layers of a multilayer object if the cut surfaces are not uniform because the quantity of transmitted light or that of reflected light changes significantly and irregular reflection occurs there. Another problem of the above described system and method is that, as the number of layers of the multilayer object increases, the area that needs to be irradiated by the first projector increases so that at least either the first projector or the optical receiver has to be moved in a direction of rectangularly crossing the layers particularly when the number of layers is large.

On the other hand, in the case of the above described known system and method for checking the number of cards, the cards to be checked have to have at least a metal foil layer or a metal oxide layer laid on part or all of the surface thereof. Additionally, they require a data base storing data on the output waveforms corresponding to the respective numbers of cards in advance because the number of layers of a multilayer object is determined by comparing the output waveforms of the reflected wave receiving sensor and the transmitted wave receiving sensor that illustrate the change with time of the output voltage values produced respecrtively by the reflected wave and the transmitted wave of the electromagnetic wave irradiated onto the cards, with the output waveforms (reference patterns) obtained from certain numbers (0 to 4) of cards as stored in advance. Furthermore, the output waveform of the electromagnetic wave that is irradiated on the the cards, that of the reflected wave and that of the transmitted wave are required to be reproducible. In short, same conditions need to be maintained always for checking the number of cards.

In view of the above identified problems, according to the present invention, there is provided a system for counting the number of layers of a multilayer object, comprising oscillation means for emitting an electromagnetic wave to strike either the top surface or the bottom surface of an object in a multilayer state (multilayer object), reception means for receiving electromagnetic waves generated by reflection of the electromagnetic wave at the interfaces of the layers of the multilayer object, and processing means for counting the number of layers of the multilayer object on the basis of signals of the reflected electromagnetic waves obtained by the reception means.

In another aspect of the invention, there is provided a system for counting the number of layers of a multilayer object, comprising oscillation means for emitting an electromagnetic wave to strike either the top surface or the bottom surface of an object in a multilayer state (multilayer object), reception means for receiving an transmitted wave generated by transmission of the electromagnetic wave through the layers of the multilayer object, and processing means for detecting a phase shift of the transmitted wave relative to the electromagnetic wave before striking the multilayer object and counting the number of layers of the multilayer object on the basis of the phase shift.

In order to dissolve the above identified problems, a system for counting the number of layers of a multilayer object according to the invention is adapted to count the number of layers of a multilayer object by means of an electromagnetic wave having a spatial resolution good for the thickness of a multilayer object (typically several millimeters to several micrometers) that can easily be transmitted through the multilayer object from the top surface to the bottom surface thereof. According to the invention, the number of layers of a multilayer object can be detected by irradiating an electromagnetic wave pulse onto a multilayer object and counting the number of layers of the multilayer object on the basis of the number of reflected (echo) pulses generated as a result of the irradiation of an electromagnetic wave pulse. According to the invention, it is also possible to know the number of layers of a multilayer object by oscillating a continuous electromagnetic wave and analyzing/processing an electromagnetic wave transmitted through the multilayer object as detected by the reception means so as to count the number of layers of the multilayer object or detecting a phase shift of the transmitted wave relative to the electromagnetic wave before striking the multilayer object so as to count the number of layers of the multilayer object. Thus, a system for counting the number of layers of a multilayer object according to the invention differs from the known method and system for checking the number of cards that is adapted for counting the number of cards on the basis of the output waveforms of reflected waves or the output waveform of the transmitted wave, each of which illustrates the change with time of the amplitude/intensity of the output. An electromagnetic wave of the above described wavelength range typically contains a tera-hertz component that is in the unexplored tera-hertz frequency range, although oscillation techniques and detection techniques have been developed in recent years for such electromagnetic waves.

The present invention can be carried out in different modes as described below.

Preferably, a system for counting the number of layers of a multilayer object according to the invention further comprises, in addition to the reception means for receiving electromagnetic waves generated by reflection, second reception means for receiving an electromagnetic wave generated by transmission of the electromagnetic wave through the multilayer object and second processing means for detecting a phase shift of the transmitted wave relative to the electromagnetic wave before striking the multilayer object and counting the number of layers of the multilayer object on the basis of the phase shift. With this arrangement, the accuracy of counting the number of layers is improved by comparing the number of layers of the multilayer object as counted on the basis of the signals of the electromagnetic waves generated by reflection of the electromagnetic wave and the number of layers obtained by the second processing means.

Preferably, a system for counting the number of layers of a multilayer object according to the invention further comprises dividing means for dividing the electromagnetic wave radiated from the oscillation means into a first electromagnetic wave for striking the multilayer object and a second electromagnetic wave to be propagated directly to the reception means or the second reception means so as to be able to supply the transmitted wave and the electromagnetic wave that does not strike the multilayer object.

Preferably, a system for counting the number of layers of a multilayer object according to the invention further comprises propagation means for propagating an electromagnetic wave either through a propagation route to the reception means or through a propagation route to the second reception means so as to minimize a loss to the electromagnetic wave oscillated by the oscillation means and propagated to the reception means.

The oscillation means may be adapted to oscillate a continuous electromagnetic wave and the number of layers of the multilayer object may be counted by analyzing/processing an electromagnetic wave transmitted through the multilayer object and detected by the reception means. The continuous wave may be modulated to use a synchronous detection method. The reception means may be so configured as to perform the analyzing/processing operation or the processing means may be adapted to perform the analyzing/processing operation by processing electric signals.

When the oscillation means is adapted to oscillate a continuous electromagnetic wave, the reception means has an antenna for receiving the electromagnetic wave directly transmitted from the oscillation means (to be also referred to as reference wave) and the electromagnetic waves generated by the electromagnetic wave as a result of being reflected by the multilayer object and additionally contains a difference amplifier for determining the difference between them and a phase difference detector for detecting phase differences from the output of the difference amplifier. The phase difference signal representing the detected phase differences is transmitted to the processing means (processor) and the processing means (processor) determines the number of layers.

Electromagnetic waves generated as a result of reflection of the electromagnetic wave by the multilayer object show respective phases that are shifted from each other as a function of the number of layers of the multilayer object so that the phase difference detector detects the phase differences, the number of which may vary as a function of the member of layers of the multilayer object. For example, when sheets of paper having an identical thickness of d are laid one on the other as shown in FIG. 1, the electromagnetic waves generated as the incident electromagnetic wave is reflected by the sheets show respective phases that are shifted by a distance twice as long as the thickness of each sheet to differentiate the lengths of the light paths. More specifically, the phases of the reflected waves are differentiated by $4\Pi nd/\lambda$ (n: the refractive index of the multilayer object 12, $\lambda$: the wavelength of the electromagnetic wave) and the phase difference detector detects phase differences, each of which is equal to $4\Pi nd/\lambda$ or integer times of $4\Pi nd/\lambda$. The number of the integers as detected by the phase difference detector represents the number of layers of the multilayer object.

The second reception means for receiving the transmitted wave also has an antenna for receiving the reference wave and the electromagnetic waves generated by the incident electromagnetic wave as a result of being transmitted through the multilayer object and contains a phase difference detector.

Since the phase of the incident electromagnetic wave is shifted each time it is transmitted through a layer of the multilayer object, the phase difference of the transmitted wave generated by the incident electromagnetic wave as a result of being transmitted through the multilayer object reflects the number of layers of the multilayer object. The phase difference detector mixes the reference wave, which is the electromagnetic wave coming directly from the oscillation means, and the received wave signals to produce an intermediate frequency and subsequently analyzes the phase differences by means of Fourier analysis in order to detect the phase differences of the received wave signals relative to the reference wave and count the number of layers. A technique of interference instrumentation may be used as means for phase difference analysis.

As described above, it is preferable to use an electromagnetic wave oscillated by the oscillation means and having a wavelength in a range from millimeters to the tera-hertz range (30 GHz to 100 THz) or containing a component having a wavelength in a range from millimeters to the tera-hertz range (30 GHz to 100 THz) that is substantially equal to the typical thickness of a multilayer object for counting the number of layers of such an object for the purpose of the present invention.

Additionally, according to the invention and in view of the above identified problems, there is provided a method for counting the number of layers of a multilayer object, comprising an oscillation step of emitting an electromagnetic wave to strike either the top surface or the bottom surface of a multilayer object, a reception step of receiving electromagnetic waves generated by reflection of the electromagnetic wave at the interfaces of the layers of the multilayer object, and a processing step of counting the number of layers of the multilayer object on the basis of signals of the reflected electromagnetic waves obtained by the reception step.

In another aspect of the invention, there is provided a method for counting the number of layers of a multilayer object, comprising an oscillation step of emitting an electromagnetic wave to strike either the top surface or the bottom surface of a multilayer object, a reception step of receiving the electromagnetic waves generated by transmission of the electromagnetic wave through the layers of the multilayer object, and a processing step of detecting a phase shift of the transmitted wave relative to the electromagnetic wave before striking the electromagnetic object and counting the number of layers of the multilayer object on the basis of the phase shift. Preferable examples of the multilayer object include nonpolar substances such as paper, plastics, and the like.

Thus, the present invention provides an advantage that the number of layer of an object in a multilayer state can be counted instantaneously by means of a simple arrangement of emitting an electromagnetic wave to strike either the top surface or the bottom surface of the object and a technique of using either reflection or transmission of the electromagnetic wave. The number of layers of a multilayer object can be counted more accurately if both the reflection method and the transmission method are used independently and simultaneously for comparison with each other.

BEST MODE FOR CARRYING OUT THE INVENTION

Now, the present invention will be described by referring to the accompanying drawings that illustrate preferred embodiments of system and method for counting the number of layers of a multilayer object by means of an electromagnetic wave. Throughout the drawings, the same elements or parts are denoted by the same reference symbols.

Embodiment 1

Figure 1:
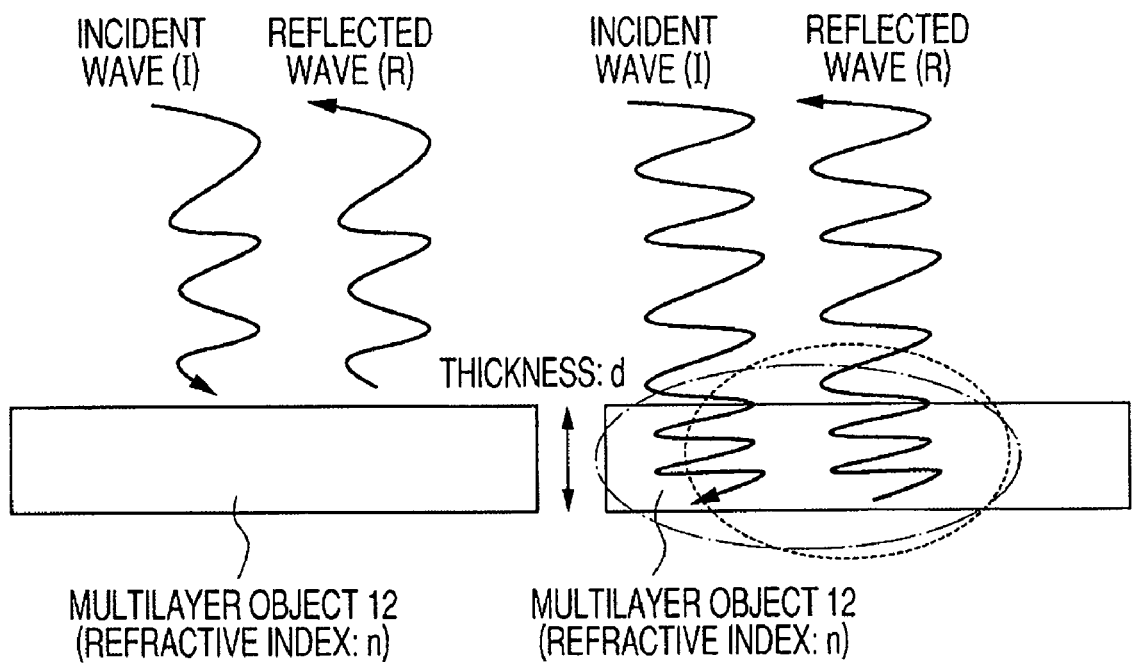
FIG. 1 is a schematic illustration of the phase difference between two reflected waves that is produced when a continuous electromagnetic wave is irradiated onto a multilayer object.
Figure 2:
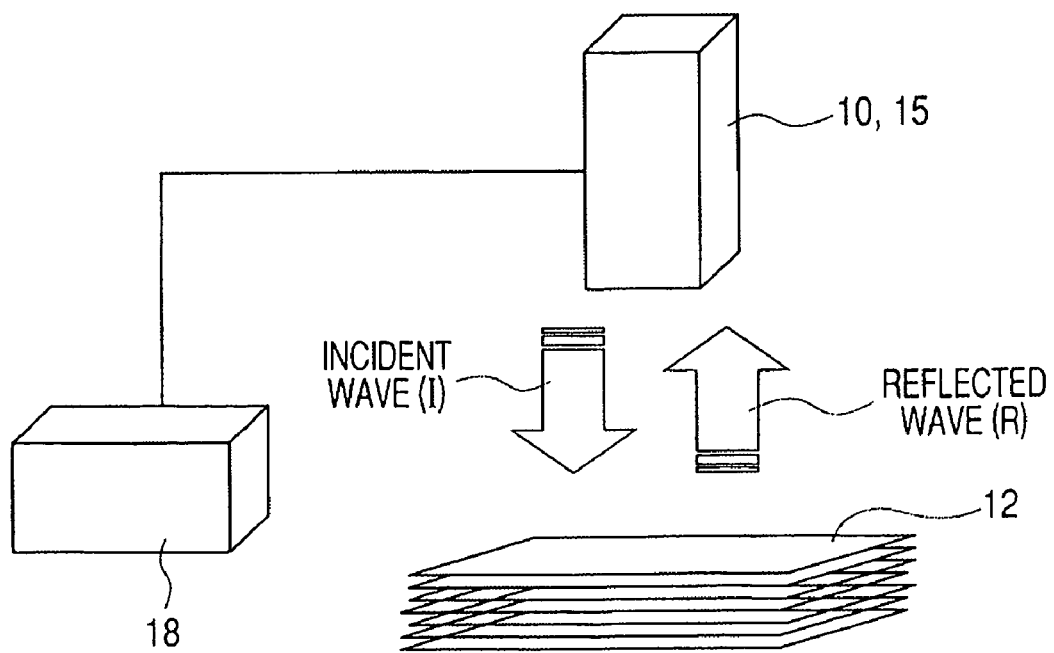
FIG. 2 is a schematic illustration of a system for counting the number of layers of a multilayer object, using the reflection method, showing the configuration thereof.

FIG. 2 is a schematic illustration of the first embodiment of system for counting the number of layers of a multilayer object according to the invention, using the reflection method, showing the configuration thereof. A single pulse electromagnetic wave (incident wave (I)) is emitted from an oscillator 10 to strike at least the top surface or the bottom surface of a multilayer object 12 that is in a state where two or more than two layers are laid one on the other and the reflected waves (R) generated at the interfaces of the intermediate layers of the multilayer object 12 are received by an optical receiver 15. The received voltage signals of the reflected waves (R) that are received by the optical receiver 15 are delivered to processing unit 18, which processing unit 18 operates to count the number of the received voltage signals.

A specific example of counting the number of sheets of paper that are laid one on the other in air will be discussed below. While both the oscillator 10 and the optical receiver 15 are realized as a single element in this example, the oscillator 10 and the optical receiver 15 may alternatively be realized as different elements. Since the multilayer object 12 of this example is that of sheets of paper, preferably a tera-hertz electromagnetic wave having a wavelength within the range of thickness of a sheet of paper (tens of several μm to hundreds of several μm) is emitted from the oscillator 10.

A preferable example of the oscillator 10 (optical receiver 15) is a photoconductive cell having a dipole antenna or a bow tie antenna. A technique of opening and closing a photoconductive switch by means of a short pulse laser may typically be used for oscillating a single pulse electromagnetic wave. More specifically, while a non-doped GaAs layer that is prepared by means of low temperature growth normally shows a high resistance, photo-carriers are generated only at an instant when the gap of the photoconductive switch is irradiated by a laser beam so that an electric current flows only for an instant if a voltage is applied to the opposite ends of the gap to generate a high frequency pulse. This phenomenon is utilized to generate a single pulse electromagnetic wave. An electromagnetic wave in a tera-hertz range is emitted by appropriately defining the pulse width of the pulse laser. While a mode-lock laser using titanium sapphire is highly controllable and hence easy to handle as pulse laser, a downsized semiconductor mode-lock laser may preferably be used when portability has high priority.

Figure 3:
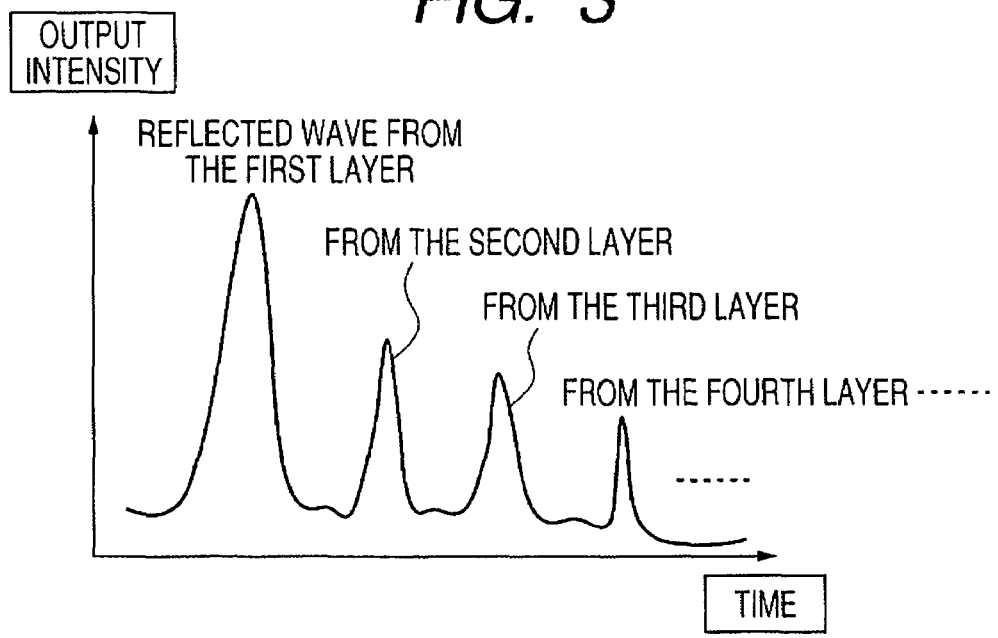
FIG. 3 is a schematic illustration of the output voltage waveform of a reflected wave produced by a multilayer object observed in an example.

FIG. 3 is a schematic illustration of the output voltage waveform that can be observed at the optical receiver 15 of this example. As an electromagnetic wave is emitted to strike at least either the top surface or the bottom surface of sheets of paper that are laid one on the other to produce a multilayer object, the electromagnetic wave is reflected by the interfaces of the sheets of paper and air. Therefore, as shown in FIG. 3, reflected wave (R) voltage signals that show the number of sheets of paper that are laid one on the other to form a multilayer object is observed.

The received voltage signals as observed at the optical receiver 15 are delivered to the processing unit 18, which processing unit 18 then conducts a temporal sampling operation on the output value of the received voltage signals at every appropriately selected split time (Ts). The temporal sampling operation is continued for a predetermined duration of time (Tf) Note that the split time (Ts) for the temporal sampling operation needs to be shorter than the time necessary for the electromagnetic wave to proceed between layers of the multilayer object 12 and the pulse width of the output temporal waveform of the reflected wave. In the case of the example where the multilayer object 12 is formed by sheets of paper, the split time (Ts) is preferably between hundreds of several femto-seconds and several pico-seconds. The duration of time (Tf) of the temporal sampling operation is appropriately defined before the start of the measurement. The split time of the temporal sampling operation may also be appropriately defined before the start of the measurement by taking the characteristics of the multilayer object into consideration.

The number of layers of the object of sheets of paper in a multilayer state can be counted as a result of the above counting sequence. The accuracy of counting can be improved by repeating the above described counting sequence or by conducting a number of similar counting operations, using a plurality of oscillation and optical reception means, and collating the obtained measurement data for verification.

Embodiment 2

Figure 4:
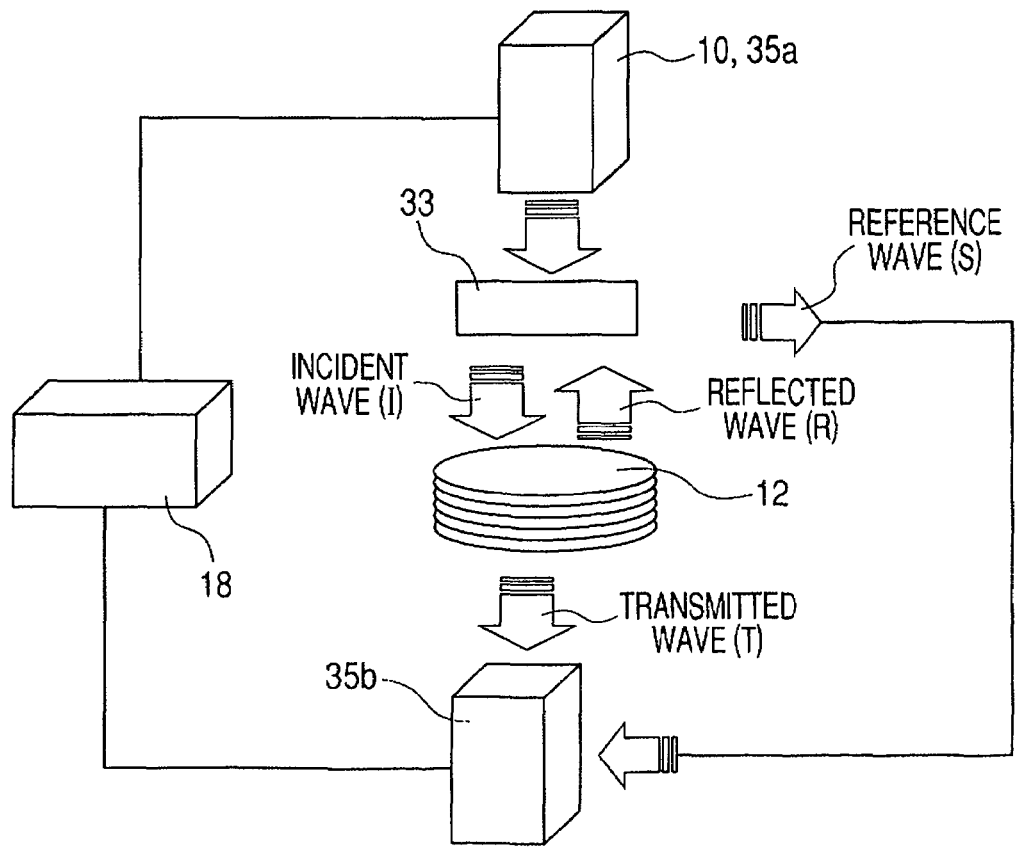
FIG. 4 is a schematic illustration of a system for counting the number of layers of a multilayer object, using both the reflection method and the transmission method, showing the configuration thereof.

FIG. 4 is a schematic illustration of the second embodiment of system for counting the number of layers of a multilayer object, using both the reflection method and the transmission method, showing the configuration thereof. An electromagnetic wave emitted from an oscillator 10 is divided into an electromagnetic pulse (incident wave (I)) adapted to strike at least the top surface or the bottom surface of a multilayer object 12 that is in a state where two or more than two layers are laid one on the other and an electromagnetic wave (reference wave (S)) that is directly propagated to second optical receiver 35b without entering the multilayer object 12. The incident wave (I) is partly reflected by the interfaces of the intermediate layers of the multilayer object 12 (to produce reflected waves (R)) and received by first optical receiver 35a. The received voltage signals generated by the reflected waves (R) received by the first optical receiver 35a are delivered to processing unit 18, which processing unit 18 operates for counting the number of layers of the multilayer object 12 on the basis of the number of the received voltage signals received by the processing unit 18.

Meanwhile, the incident wave (I) is partly transmitted through the multilayer object 12 (to become a transmitted wave (T)) and received by the second optical receiver 35b. The second optical receiver 35b detects the phase difference between the transmitted wave (T) and the reference wave (S) and the obtained data is delivered to the processing unit 18, which processing unit 18 counts the number of, layers of the multilayer object 12 from the phase difference between the transmitted wave (T) and the reference wave (S). The processing unit 18 then compares the number of layers of the multilayer object 12 as counted on the basis of the reflected waves (R) and the number of layers of the multilayer object 12 as counted on the basis of the transmitted wave (T) and outputs the outcome of the counting operation.

Now, a specific example of counting the number of recording mediums (e.g., compact disks) that are laid one on the other in air will be discussed below. While both the oscillator 10 and the first optical receiver 35a are realized as a single element also in this example, the oscillator 10 and the first optical receiver 35a may alternatively be realized as different elements. For instance, in FIG. 4, the oscillator 10 is shown as a different element than element 33, which in this instance, represents the first optical receiver.

The received voltage signals of the reflected waves (R) as observed at the first optical receiver 35a of this example are similar to those of the reflected waves (R) as observed in the first embodiment and shown in FIG. 3. The counting method of this example is substantially same as that of the first embodiment. This example differs from the first embodiment in that, since the multilayer object 12 of this example is that of recording mediums and has a thickness of tens of several times of the multilayer object 12 of sheets of paper of the above described embodiment, preferably an electromagnetic wave having a wavelength of tens of several times of the electromagnetic wave for counting the number of sheets of paper, or a millimeter wave or a tera-hertz wave, is emitted from the oscillator 10 and that the split time (Ts) of the temporal sampling operation is preferably between several pico-seconds and hundreds of several pico-seconds.

The transmitted wave (T) that is received by the second optical receiver 35b shows a phase shift of a constant amount each time it is transmitted through a layer in the layers of recording mediums that are in a multilayer state. Therefore, the number of layers of recording mediums is determined by comparing the phase of the transmitted wave (T) and that of the reference wave (S) that is not transmitted through the recording mediums and directly received by the second optical receiver 35b and detecting the phase shift of the transmitted wave (T) relative to the electromagnetic wave prior to striking the recording mediums.

Figure 5:
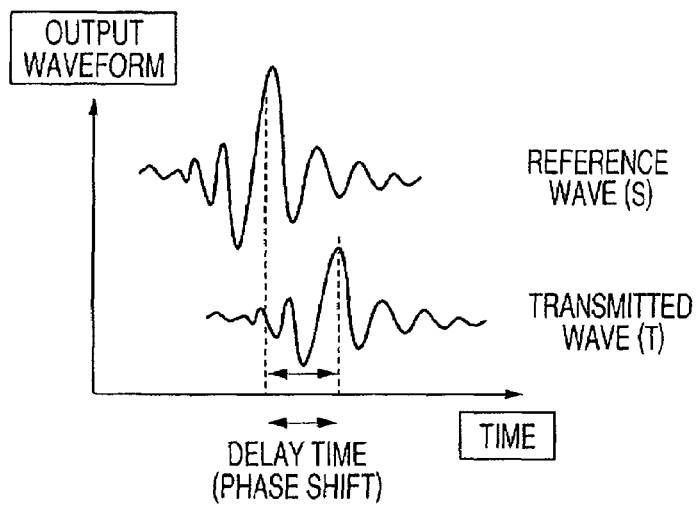
FIG. 5 is a graph illustrating the output voltage waveform of a transmitted wave transmitted through a multilayer object and that of an electromagnetic wave (reference wave) before striking the multilayer object, showing the relative phase shift between them.

FIG. 5 is a graph illustrating a typical example of output voltage waveform of a transmitted wave (T) transmitted through a multilayer object 12 and that of output voltage waveform of an electromagnetic pulse detected when there is no multilayer object 12. The two waveforms are drawn by using the clock time when a sweeping operation is started for sampling as reference. For example, since the time difference between the detected peak voltages of the two waveforms (which corresponds to the delay time or the relative phase shift between the two electromagnetic pulses) changes discretely as a function of the number of layers of the multilayer object 12, the number of layers of the multilayer object 12 can be determined by detecting the time difference (phase shift). It may be needless to say that the same result is obtained by detecting the time difference between arbitrarily selected two points on the two waveforms that show a same voltage value as well as not by detecting the peak voltages.

Subsequently, the processing unit 18 judges if the number of layers of the recording mediums as determined from the reflected waves (R) and the number of layers of the recording mediums as determined from the transmitted wave (T) agree with each other. If they agree with each other, the counting sequence is taken into account and the determined number of layers is stored. If they do not agree with each other, on the other hand, the counting sequence is not taken into account but the number of layers as determined from the reflected waves (R) and the transmitted wave (T) are stored.

Figure 6:
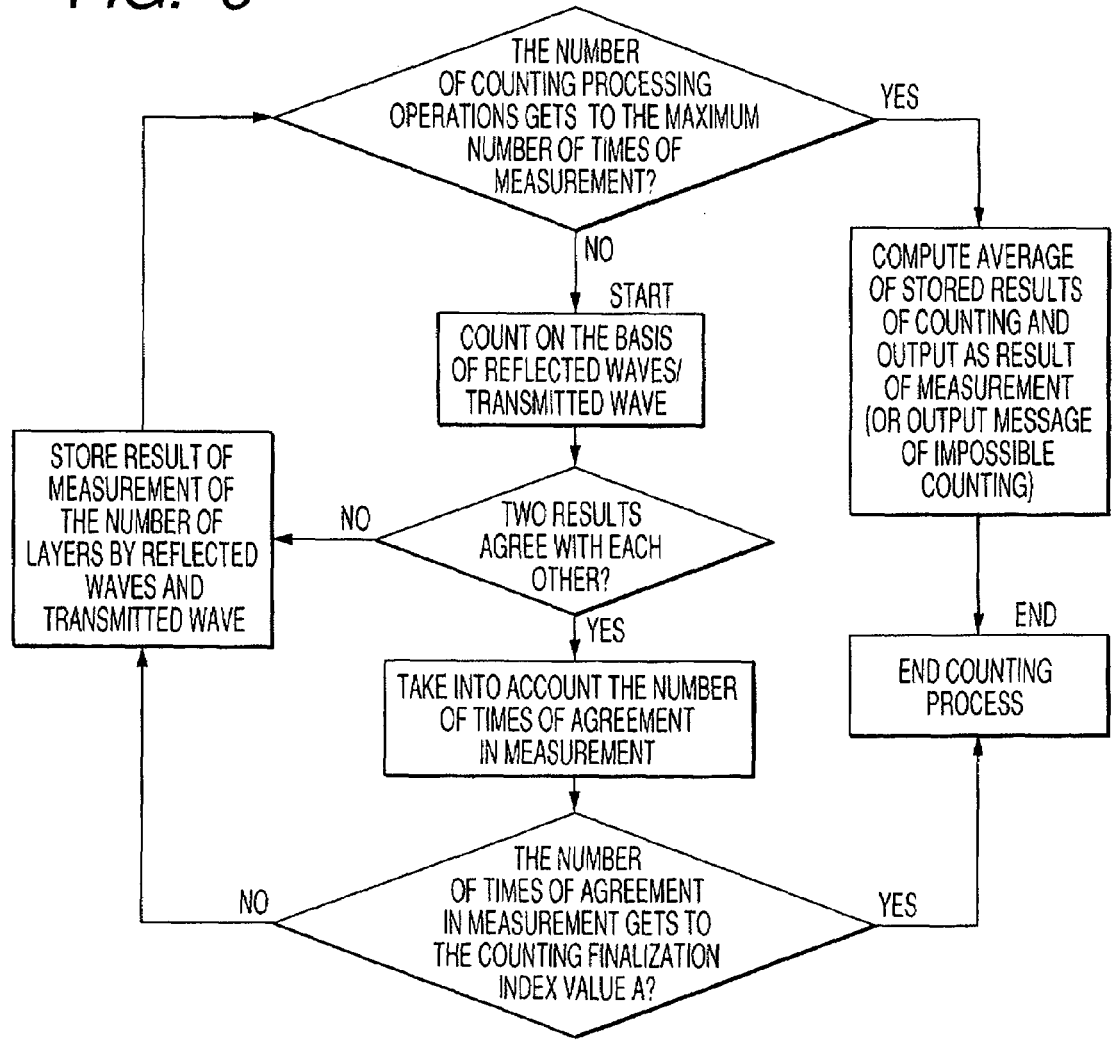
FIG. 6 is a flow chart of the counting operation of a system for counting the number of layers of a multilayer object, using both the reflection method and the transmission method.

The processing operation of the counting sequence for counting the number of recording mediums by means of both the reflection method and the transmission method will be described by referring to the flow chart of FIG. 6. In this example, the counting sequence is repeated maximally up to the limit number of times of measurement M, which is arbitrarily selected. If the number of layers counted by the reflection method agrees with the number of layers counted by the transmission method in a counting session, the number of times of agreement for that number of layers is incremented by one. The counting operation is terminated when the number of times of agreement gets to a predetermined counting finalization index value A and that number of layers is output as the result of measurement.

If the counting sequence is repeated for the limit number of times of measurement M without getting to the predetermined counting finalization index value A, the average of the numbers of layers counted by the reflection method and the transmission method and stored is computed and output as the result of measurement or a message of impossible counting is output because the counting is not accurate.

In the above-described example, it is possible to provide a database for storing the output waveform of the reference wave (S) that is used in the counting sequence and the data stored in the data base is delivered to the processing unit 18. With this arrangement, it is not necessary to propagate the reference wave (S). The arrangement of using both the reflection method and the transmission method as in the case of the above-described example (or using only the transmission method) is suitable when the layers of the object in a multilayer state are identical or when the types of and the mode of laying the layers are known in advance and hence the phase shift that arises each time the electromagnetic wave passes through a layer is also known. To the contrary, the first embodiment is a general purpose counting system and not subject to limitations so long as the object of counting generates reflected wave voltage signals because the layers of the object are counted by observing the reflected wave (R) voltage signals that represent the layers of the multilayer object.

While this embodiment uses both the reflection method and the transmission method, it may be needless to say that the number of layers of a multilayer object 12 can be counted only by using the transmission method. When only the transmission method is used, the first optical receiver 35a of the above described example is not necessary. In other words, a simpler arrangement is used to count the number of layers of a multilayer object 12.

It is also possible to use a plurality of units of the oscillator 10, the first optical receiver 35a and the second optical receiver 35b and arranging the oscillators 10 at appropriate positions at the top surface side and/or at the bottom surface side for measurement.

Embodiment 3

Figure 7:
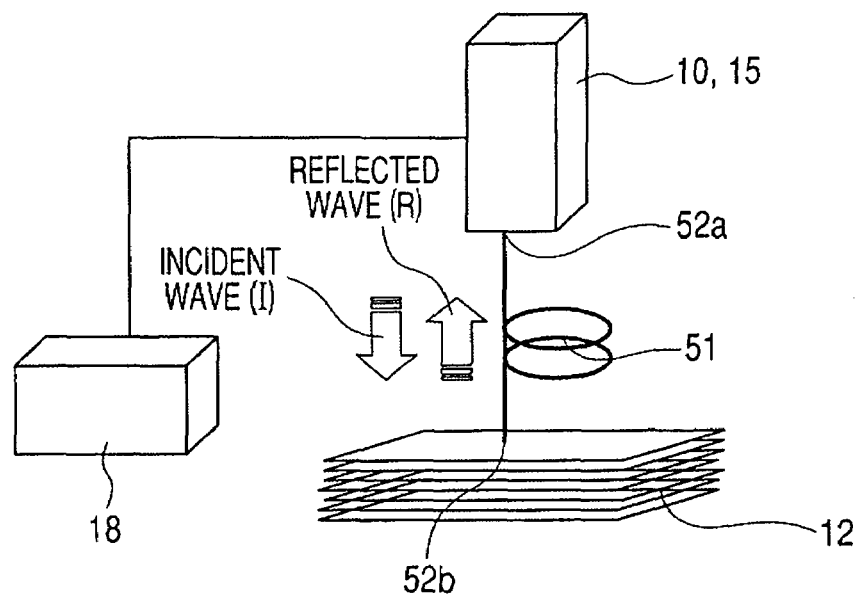
FIG. 7 is a schematic illustration of a system for counting the number of layers of a multilayer object using a propagation path and the reflection method, showing the configuration thereof.

FIG. 7 is a schematic illustration of a system for counting the number of layers of a multilayer object using a propagation path with the reflection method described above by referring to the first embodiment, showing the configuration thereof. This embodiment differs from the first embodiment only in that the electromagnetic wave emitted from the oscillator 10 is partly or entirely made to be propagated to the optical receiver 15 by way of a propagation path. Otherwise, this embodiment is identical with the first embodiment.

A specific example of counting the number of sheets of paper that are laid one on the other in air will be discussed below. In this example using the above described reflection method, both the electromagnetic wave that is propagated through air to strike the sheets of paper and the electromagnetic wave that is propagated through air from the surface of the sheets of paper at the side of the optical receiver 15 to the optical receiver 15 are propagated partly or entirely by way of a propagation path. A front end section 52a of a propagation path is connected to the electromagnetic emitting section including the oscillator 10 that emits an electromagnetic wave and the other front end section 52b of the propagation path is held in contact with and rigidly secured to the top surface of the layers of sheets of paper that are laid one on the other. The oscillator 10 is made to oscillate and emit an electromagnetic wave in this condition. The electromagnetic wave reflected by the sheets of paper is propagated from the rigidly secured front end section 52b to the front end section 52a of the propagation path 51 and received by the optical receiver 15. However, it is not necessary to make the front end section 52b of the propagation path 51 to be held in contact with the top surface of the layers of sheets of paper and may alternatively be separated from the latter for measurement.

Embodiment 4

Figure 8:
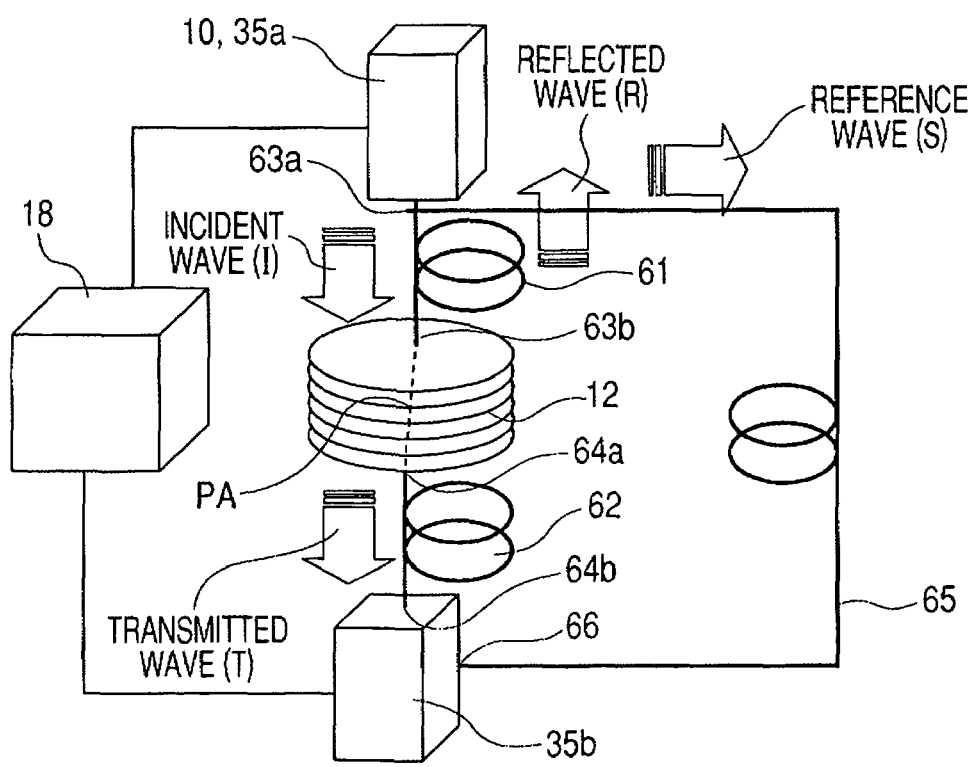
FIG. 8 is a schematic illustration of a system for counting the number of layers of a multilayer object, using a propagation path and both the reflection method and the transmission method, showing the configuration thereof.
Figure 9:
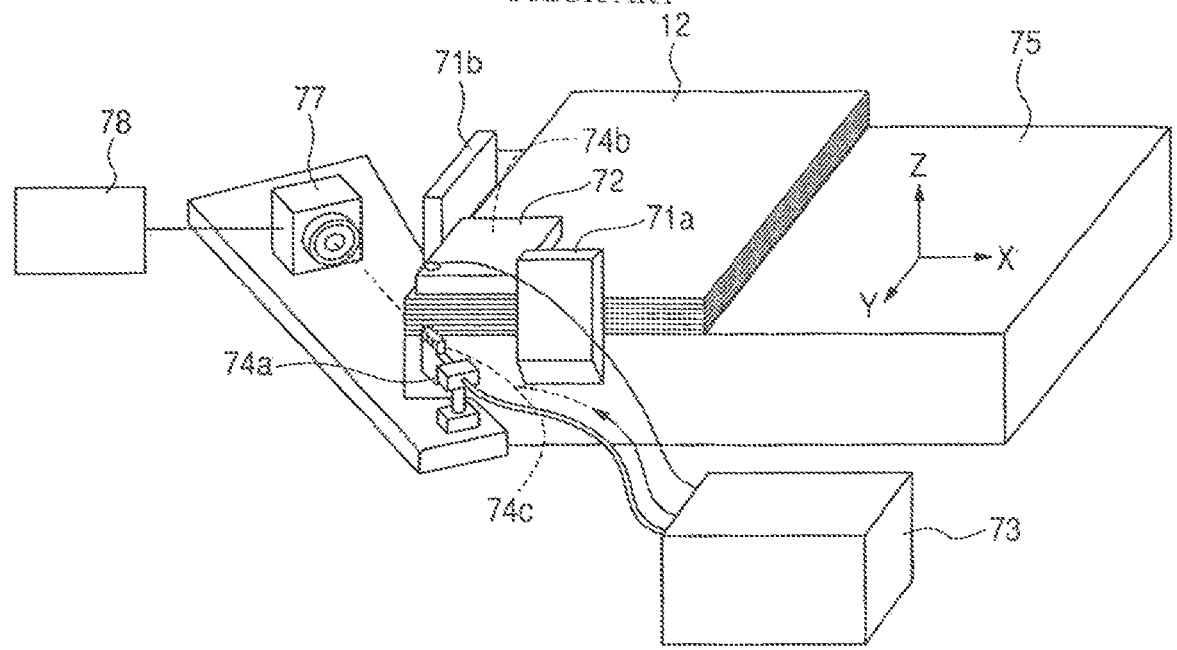
FIG. 9 is a schematic illustration of a known system for counting the number of layers of a multilayer object by irradiating light onto a lateral surface of the object.
Figure 10:
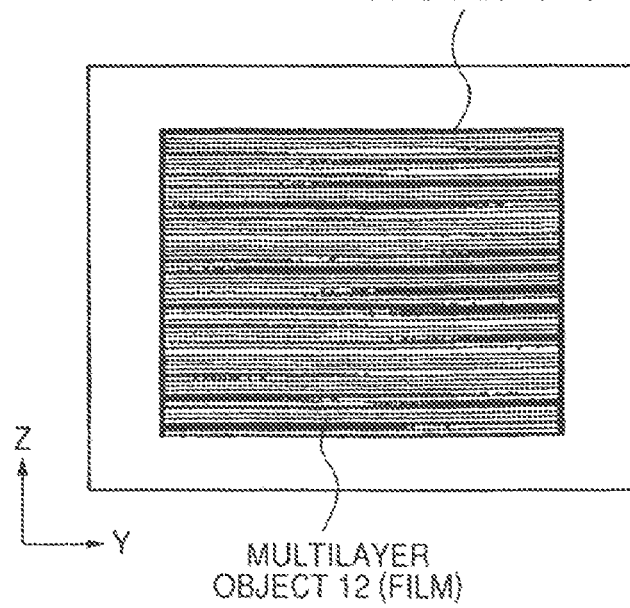
FIG. 10 is a schematic illustration of the image information on the distribution of the intensity of light relative to the Z-axis as detected by an optical receiver.
Figure 11:
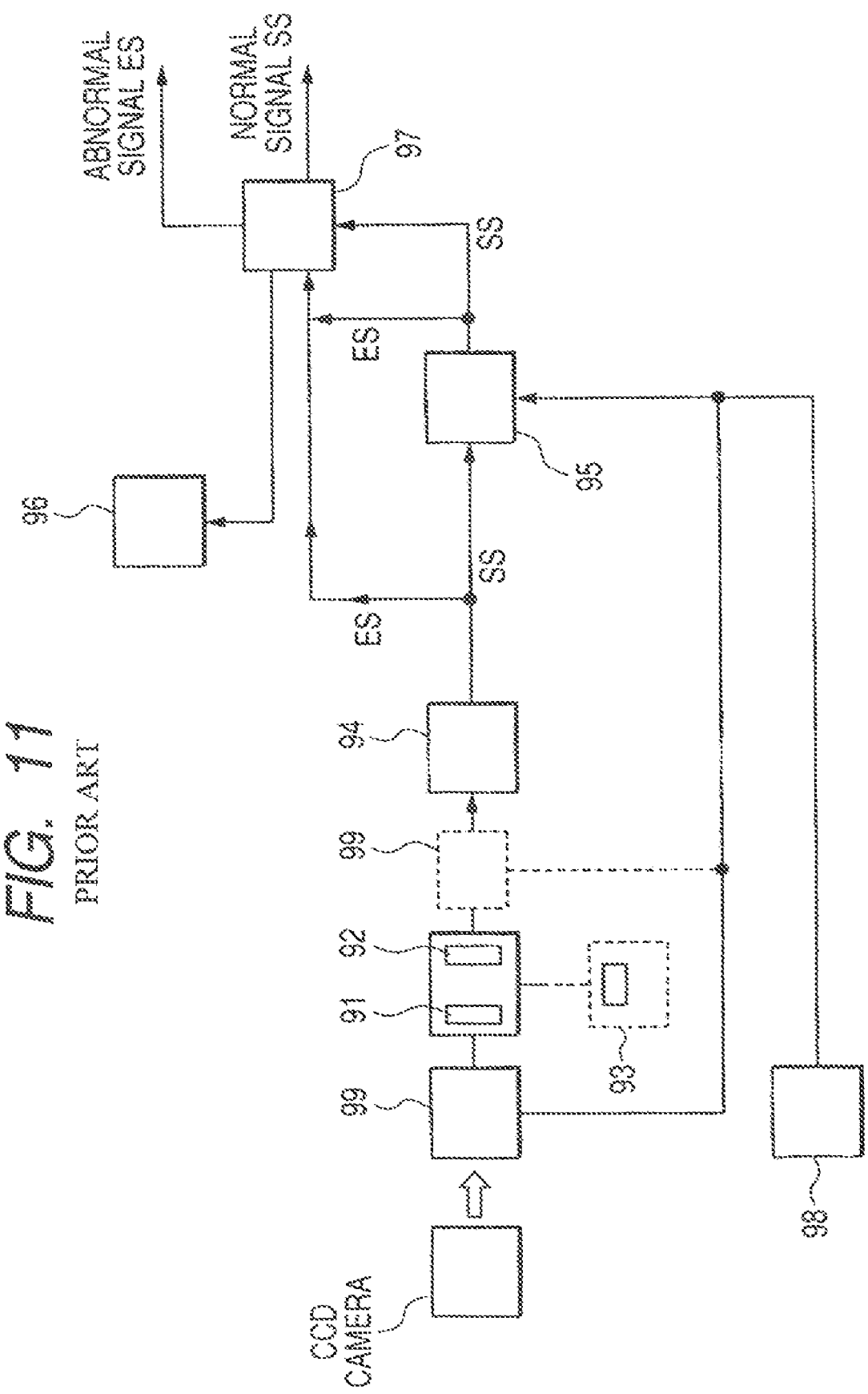
FIG. 11 is a schematic block diagram of a known system for counting the number of cards laid one on the other and contained in an envelope in a sealed state.
Figure 12A:
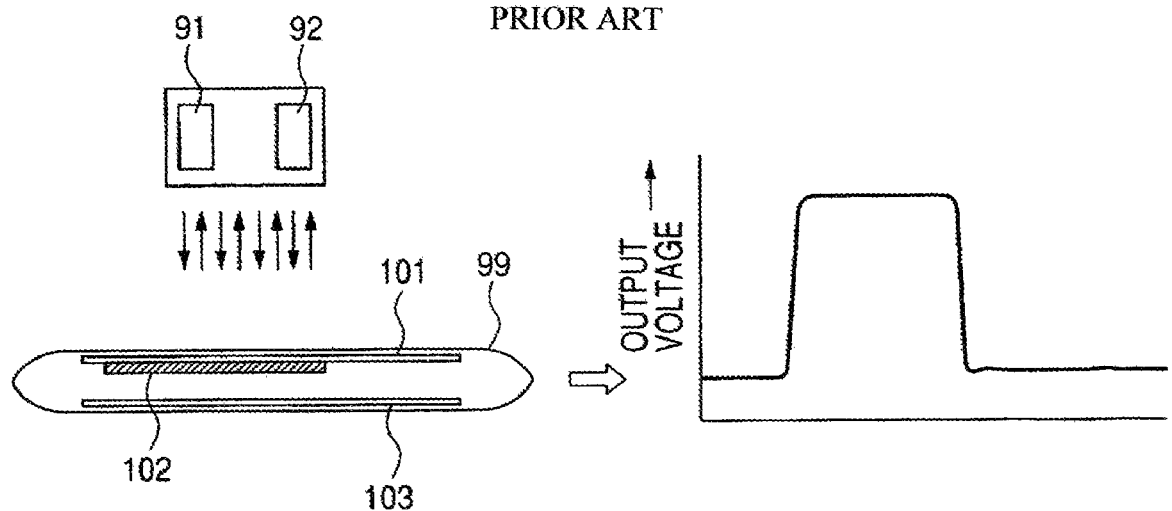
FIGS. 12A and 12B are schematic illustrations of a known system for counting the number of cards by means of a reflected wave generated by an electromagnetic wave and an exemplary output waveform of the system (FIG. 12A) and the exemplary waveform of a reflected wave of the system that is obtained when the envelope does not contain any card therein (FIG. 12B).
Figure 12B:
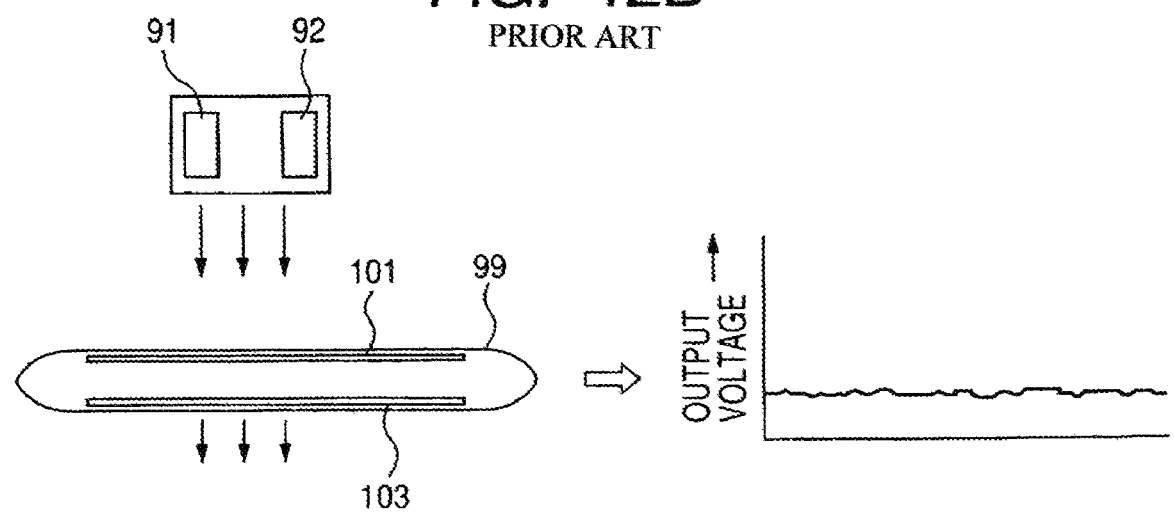

FIG. 8 is a schematic illustration of a system for counting the number of layers of a multilayer object, using propagation paths and both the reflection method and the transmission method as in the case of Embodiment 2, showing the configuration thereof. The electromagnetic wave that is emitted from the oscillator 10 is propagated through first propagation path 61 and subsequently an incident electromagnetic pulse (incident wave (I)) is emitted at least onto the top surface or onto the bottom surface of an object that is in a state where at least two layers are laid one on the other (a multilayer object 12). The reflected waves (R) that are generated by the incident electromagnetic pulse as the latter and that is reflected at the interfaces of the layers of the multilayer object 12 are propagated through the first propagation path 61 and received by the first optical receiver 35*a*. The received voltage signals produced by the reflected waves (R) and received by the first optical receiver 35*a* are delivered to the processing unit 18, which processing unit 18 counts the number of the layers on the basis of the received electromagnetic pulses.

On the other hand, the transmitted wave (T) that is transmitted through the multilayer object 12 is propagated through second propagation path 62 and subsequently received by the second optical receiver 35*b*. The phase shift of the transmitted wave (T) relative to the reference wave that is produced as a result of transmission of the wave through the multilayer object 12 is determined by comparing the output waveform of the transmitted wave (T) that is received by the second optical receiver 35*b* and the output waveform of the reference wave (S) that is propagated through third propagation path 65, which third propagation path 65 is formed by branching the first propagation path 61. The data obtained as a result of comparison is delivered to the processing unit 18 for the purpose of counting the number of layers of the multilayer object 12. Additionally, the processing unit 18 compares the number of layers of the multilayer object 12 counted on the basis of the reflected waves (R) and the number of layers of the multilayer object 12 counted on the basis of the transmitted wave (T) and processes them for validation to output the outcome of the counting operation.

Now, a specific example of counting the number of recording mediums (e.g., compact disks) that are laid one on the other in air will be discussed below. In this example of using both the reflection method and the transmission method, the front end section 63*a* of the first propagation path 61 is fitted to the electromagnetic wave emitting section of the oscillator 10 and the other front end section 63*b* is held in contact with and rigidly secured to the top surface of the recording mediums. Before emitting an electromagnetic wave from the oscillator 10, the front end section 64*a* of the second propagation path 62 is held in contact with and rigidly secured to the intersection of the electromagnetic wave propagation axis PA, which is the propagation route of the electromagnetic wave emitted from the front end section 63*b* of the first propagation path 61 and the bottom surface of the recording mediums, and other front end section 64*b* is fitted to the receiving section of the second optical receiver 35*b*.

Additionally, the third propagation path 65 is branched from the first propagation path 61 and the front end section 66 thereof is fitted to the receiving section of the second optical receiver 35*b*. After the above preparation process, the electromagnetic wave emitted from the oscillator 10 is propagated to the top surface of the recording mediums. The reflected waves (R) generated by the electromagnetic wave as it is reflected by the interfaces of the recording mediums are propagated from the front end section 63*b* to the front end section 63*a* of the first propagation path 61 and received by the first optical receiver 35*a*. On the other hand, the transmitted wave (T) that is transmitted through the recording mediums is propagated from the front end section 64*a* of the second propagation path 62 that is fitted to the bottom surface of the recording mediums to the other front end section 64*b* and received by the second optical receiver 35*b*. The electromagnetic wave emitted from the oscillator 10 is partly transmitted as reference wave (S) through the third propagation path 65 that is branched from the first propagation path 61 to the front end section 66 thereof and received by the second optical receiver 35*b*. Since the transmitted wave (T) that is transmitted through the multilayer object 12 is propagated to expand in space, it is preferable to converge the transmitted wave to the rigidly secured front end section 64*a* of the second propagation path 62 by means of a lens arranged at the bottom surface side of the multilayer object 12. The counting operation can be conducted by following the flow chart of FIG. 6, which is described above by referring to the second embodiment.

The propagation paths that are used in the third and fourth embodiments are effective in a situation where the electromagnetic wave is subjected to a large propagation loss as in the case where the object whose number of layers is to be counted is separated from the oscillator means or the reception means and in the case where one or more than one electromagnetic wave absorbing objects such as water are found on the propagation route of the electromagnetic wave.

While the propagation paths that are used in the third and fourth embodiments may be of any type, the use of microstrip lines or propagation fibers is preferable when an electromagnetic wave in the range of millimeter wave to terahertz wave is transmitted as in the case of the above described embodiments.

While the multilayer objects of the first through fourth embodiments include those of sheets of paper and those of recording mediums, the present invention is equally applicable to multilayer objects of pieces of china or porcelain such as dishes and bowls, those of corrugated cardboards, those of plates, those of bank notes and those of other non-polar articles. The present invention may also be applicable to multilayer objects of polar articles that do not absorb the electromagnetic wave irradiating them. Then, however, the wavelength of the electromagnetic wave emitted from the oscillation means has to be changed depending on the thickness (normally up to about 1 cm) of the multilayer object that is the object of counting.

While the multilayer object that is the object of counting is located in air in the above description of the first through fourth embodiments, it does not necessarily have to be located in air. In other words, it can be subjected to a counting operation in any environment so long as the environment shows a dielectric constant that is different from the multilayer object, the interfaces of the layers of which reflect an electromagnetic wave. For example, the counting operation may be conducted in vacuum, in a nitrogen environment or some other environment.

While the multilayer object that is the object of counting is stationary in the above description of the first through fourth embodiments, the object of counting and/or the oscillation means and the reception means may be moving in the measurement system where the present invention is applied so long as the electromagnetic wave emitted from the oscillation means interacts with the multilayer object that is the object of counting interact and is received by the reception means to complete the counting sequence. For example, for counting the number of layers of a multilayer object that is being conveyed by a belt conveyor, the oscillation means and the reception means may be rigidly secured to the top surface side of the belt conveyor (and the second reception means may be arranged at the bottom surface side of the belt conveyor if necessary) and an electromagnetic wave is emitted to the multilayer object when the latter passes through the propagation route of the electromagnetic wave that is emitted from the oscillation means. Then, the number of layers of the multilayer object can be counted as in the case of the above described embodiments.

A system for counting the number of layers of a multilayer object according to the invention and described above by referring to the first through fourth embodiments can find applications in the field of printing machines and copying machines for counting the number of sheets or detecting sheets being fed in duplicate at the cassette paper feeding section, the manual paper feeding section or the original feeding section of the machine, in the field of sheets packets conveying machines for counting the number of sheets of paper being conveyed, in the field of manufacturing recording mediums such as compact disks for counting the number of recording mediums and in the field of restaurants for counting the number of dishes.

When a system for counting the number of layers of a multilayer object according to the invention and described above by referring to the first through fourth embodiments is used for counting the number of sheets of paper, it can count one to several hundreds sheets. If it is used to deal with such a wide range of number, the intensity and the frequency zone of the electromagnetic wave may have to be regulated depending on the multilayer object to be handled so that it can be transmitted through the multilayer object.

This application claims priority from Japanese Patent Application No. 2003-393248 filed on Nov. 25, 2003, which is hereby incorporated by reference herein.

The invention claimed is:

1. A system for counting the number of layers of a multilayer object, comprising:
    an oscillation unit for oscillating an electromagnetic wave having a frequency in a range from 30 GHz to 100 THz to irradiate either a top surface or a bottom surface of the multilayer object;
    a first reception unit for receiving the electromagnetic wave having pulses reflected at interfaces of the layers of the multilayer object;
    a first processing unit for counting the number of pulses of the electromagnetic wave received by the first reception unit, and counting the number of layers of the multilayer object on the basis of the counted number of pulses;
    a second reception unit for receiving the electromagnetic wave oscillated by said oscillation unit and transmitted through the multilayer object; and
    a second processing unit for counting the number of layers of the multilayer object on the basis of a delay time detected by using the transmitted electromagnetic wave,
    wherein the number of layers counted by the first processing unit is compared with the number of layers counted by the second processing unit to count the number of layers of the multilayer object.

2. The system according to claim 1, further comprising:
    a dividing unit for dividing the electromagnetic wave oscillated by said oscillation unit into a first electromagnetic wave for irradiating the multilayer object and a second electromagnetic wave to be propagated directly to said first reception unit or said second reception unit.

3. The system according to claim 1, further comprising:
    a propagation unit for propagating the electromagnetic wave oscillated by said oscillation unit through a propagation route getting to said first reception unit or said second reception unit.

4. The system according to claim 1, wherein the oscillation unit and the first and second reception units are photoconduction devices, respectively, and the temporal waveform is acquired through a terahertz time domain spectroscopy.

5. The system according to claim 1, wherein if the number of layers counted by the first processing unit is not equal to the number of layers counted by the second processing unit, an average of the number of layers counted by both the first processing unit and the second processing unit is computed.

6. A method for counting the number of layers of a multilayer object, comprising:
    an oscillation step of oscillating an electromagnetic wave having a frequency in a range from 30 GHz to 100 THz to irradiate either a top surface or a bottom surface of a multilayer object;
    a first reception step of receiving the electromagnetic wave having pulses reflected at interfaces of the layers of the multilayer object;
    a first processing step of counting the number of pulses of the electromagnetic wave received in the first reception step, and counting the number of layers of the multilayer object on the basis of the counted number of pulses;
    a second reception step of receiving the electromagnetic wave oscillated in said oscillation step and transmitted through the multilayer object; and
    second processing step of counting the number of layers of the multilayer object on the basis of a delay time detected by using the transmitted electromagnetic wave,
    wherein the number of layers counted in the first processing step is compared with the number of layers counted in the second processing step to count the number of layers of the multilayer object.

7. The method according to claim 6, wherein if the number of layers counted in the first processing step is not equal to the number of layers counted in the second processing step, an average of the number of layers counted in both the first processing step and the second processing step is computed.

8. A system for counting the number of layers of a multilayer object, comprising:
    an oscillation unit for oscillating an electromagnetic wave having a frequency in a range from 30 GHz to 100 THz to irradiate either a top surface or a bottom surface of the multilayer object;
    a reception unit for receiving the electromagnetic wave having pulses reflected at interfaces of the layers of the multilayer object; and
    a processing unit for counting the number of layers of the multilayer object on the basis of the number of pulses, which is counted by using output values of the reflected electromagnetic wave by sampling
    output values of the reflected electromagnetic wave pulses at every split time, said split time being shorter than a pulse width of a temporal waveform of the reflected electromagnetic wave,
    wherein the sampling is performed for a predetermined amount of time.

9. The system according to claim 8, wherein the oscillation unit or the reception unit is comprised of a photoconductive switch, and the temporal waveform is acquired through a terahertz time domain spectroscopy.

10. The system according to claim 8, wherein an object comprised in the multilayer object is within a range of tens of several μm to hundreds of several μm in thickness.

11. The system according to claim 8, wherein said split time is shorter than a time necessary for the electromagnetic wave to proceed between layers of the multilayer object.

12. A method for counting the number of layers of a multilayer object, comprising:
    an oscillation step of oscillating an electromagnetic wave having a frequency in a range from 30 GHz to 100 THz to irradiate either a top surface or a bottom surface of a multilayer object;
    a reception step of receiving the electromagnetic wave having pulses reflected at interfaces of the layers of the multilayer object; and
    a processing step of counting the number of layers of the multilayer object on the basis of the number of pulses, which is counted by using output values of the reflected electromagnetic wave by sampling output values of the reflected electromagnetic wave pulses at every split time, said split time being shorter than a pulse width of a temporal waveform of the reflected electromagnetic wave, wherein the sampling is performed for a predetermined amount of time.

* * * * *